US008394045B2

(12) United States Patent
Betcher (10) Patent No.: US 8,394,045 B2
(45) Date of Patent: Mar. 12, 2013

(54) HAND HELD ORTHOSIS HAVING A FLEXIBLE ENCLOSURE AND METHOD OF UTILIZATION

(76) Inventor: Russell A. Betcher, Knoxville, TN (US)

(*) Notice: Subject to any disclaimer, the term of this patent is extended or adjusted under 35 U.S.C. 154(b) by 0 days.

(21) Appl. No.: 13/301,843

(22) Filed: Nov. 22, 2011

(65) Prior Publication Data
US 2012/0065563 A1    Mar. 15, 2012

Related U.S. Application Data

(63) Continuation of application No. 11/031,658, filed on Jan. 7, 2005, now Pat. No. 8,092,411.

(51) Int. Cl.
*A61F 5/37* (2006.01)
*A61F 13/00* (2006.01)
*A61F 5/00* (2006.01)
*A61F 13/06* (2006.01)
*A61B 19/00* (2006.01)
*A63B 23/16* (2006.01)

(52) U.S. Cl. ......... 602/21; 602/3; 602/5; 602/6; 602/20; 602/22; 602/60; 602/64; 482/49; 128/846; 128/869; 128/878; 128/879; 128/880

(58) Field of Classification Search ............. 602/3, 5–6, 602/8, 13, 21–22; 128/878–880; 482/49, 482/91, 124
See application file for complete search history.

(56) References Cited

U.S. PATENT DOCUMENTS

| 2,962,288 | A | * | 11/1960 | Lowden | 473/206 |
|---|---|---|---|---|---|
| 3,606,316 | A | | 9/1971 | Krewer | |
| 3,762,401 | A | | 10/1973 | Tupper | |
| 4,441,487 | A | | 4/1984 | Daugherty et al. | |
| 5,076,569 | A | | 12/1991 | Gooter | |
| 5,327,918 | A | | 7/1994 | Stewart et al. | |
| 5,403,008 | A | | 4/1995 | Mainiero | |
| 5,485,856 | A | | 1/1996 | Buckland | |
| 5,533,949 | A | | 7/1996 | Hwang | |
| 5,765,228 | A | | 6/1998 | Bieling | |
| 5,766,142 | A | | 6/1998 | Hess | |
| 5,820,522 | A | | 10/1998 | Smallwood et al. | |
| 5,855,209 | A | | 1/1999 | Henandez et al. | |
| 5,921,945 | A | | 7/1999 | Gray | |
| 6,482,168 | B1 | | 11/2002 | Betcher | |
| 6,663,579 | B2 | | 12/2003 | Eikanas | |

* cited by examiner

*Primary Examiner* — Michael Brown
*Assistant Examiner* — Brandon L Jackson
(74) *Attorney, Agent, or Firm* — Pitts & Lake, PC (57) ABSTRACT

A hand orthosis supporting a patient's thumb and fingers spaced apart and separated from contact with the palm of the hand, including an elongated body having a palm surface, a thumb portion, and a finger support portion. The elongated body includes a plurality of unequal cross-sectional areas spaced along the axial length between a distal end and a base end. A plurality of finger concavities are angled in helical orientation along the orthosis, including spaced apart concavities for each finger and the patient's thumb. Each finger and thumb concavity is angled non-perpendicular relative to the orthosis axial length to retain the fingers and thumb spaced apart, curved in a relaxed orientation, and apart from the palm of the hand during extended periods of time without impeding hand or wrist motion. A method of extended use for the hand orthosis is also disclosed.

3 Claims, 8 Drawing Sheets

Fig.9

HAND HELD ORTHOSIS HAVING A FLEXIBLE ENCLOSURE AND METHOD OF UTILIZATION

CROSS-REFERENCE TO RELATED APPLICATIONS

This application is a continuation of, and claims the benefit of, U.S. patent application Ser. No. 11/031,658, filed on Jan. 7, 2005, currently pending, incorporated herein by reference.

STATEMENT REGARDING FEDERALLY SPONSORED RESEARCH OR DEVELOPMENT

Not Applicable.

BACKGROUND OF THE INVENTION

1. Field of Invention

This invention pertains to a hand held orthosis for use in surgical, rehabilitative and geriatric settings. More particularly, this invention pertains to a resilient hand held orthosis positioned to maintain separation between a patient's fingers and palm during medical procedures and rehabilitative procedures relating to the patient's hands, arms, and shoulders.

2. Description of the Related Art

In the fields of hand exercising and rehabilitative procedures relating to hands, it is known that a person can maintain and strengthen the muscles of his/her hands by repeatedly gripping hand exercise devices. It is further known in the field of surgical procedures conducted on a patient's hand, wrist, arm and/or shoulder, that an anesthetized patient retains the ability to grip and sequentially contract his/her hands during surgery, thereby incurring any one or more of: deformation of fingers, formation and maintenance of a rigid fist, and/or scarring of the palmar surface by fingernails when fingers are not restrained during surgery and post-surgical recovery. Various devices have been developed to accomplish strengthening of a user's hands, but in non-surgical settings. As provided in the following U.S. patents, additional devices have been developed to maintain separation of fingers from the palm of the hand, typically by utilizing a rigid planar surface, a cylindrical body, or by positioning the fingers of a hand in a glove which separates each finger from direct contact with the palm.

| Pat. No. | Inventor(s) | Issue Date |
|---|---|---|
| 3,606,316 | S. E. Krewer | Sep. 20, 1971 |
| 3,762,401 | J. W. Tupper | Oct. 02, 1973 |
| 4,441,487 | Daugherty, et al. | Apr. 10, 1984 |
| 5,076,569 | S. M. Gooter | Dec. 31, 1991 |
| 5,327,918 | C. O. Stewart, et al. | Jul. 12, 1994 |
| 5,403,008 | J. Mainiero | Apr. 04, 1995 |
| 5,533,949 | C.-W. Hwang | Jul. 09, 1996 |
| 5,485,856 | P. E. Buckland | Jan. 23, 1996 |
| 5,765,228 | R. Bieling | Jun. 16, 1998 |
| 5,766,142 | C. E. Hess | Jun. 16, 1998 |
| 5,820,522 | P. A. Smallwood et al. | Oct. 13, 1998 |
| 5,855,209 | L. Hernandez, et al. | Jan. 05, 1999 |
| 5,921,945 | J. C. Gray | Jul. 13, 1999 |
| 6,482,168 | R. A. Betcher | Nov. 19, 2002 |
| 6,663,579 | J. Eikanas | Dec. 16, 2003 |

Of the above listed patents, the '569 issued to S. M. Gooter, discloses a contoured grip designed for short periods of exercises by repetitive squeezing and releasing by either right or left hands. The grip includes an upper, intermediate head portion against which the thumb is pressed against for strengthening exercises. The contoured grip includes a lower grip body having two mirror image halves of convex sides which lie on either side of an imaginary plane intersecting the grip body. The lower width and upper width of the grip handle are about equal, thereby providing an oval grip body having mirror image halves to allow for holding in either a right hand or a left hand, in either an upward or downwards orientation. When squeezing the grip body, the user's fingers are positioned in generally side-by-side, parallel, and touching engagement within finger indents extended across a forward portion of the grip body. The finger indents are generally perpendicular to the length axis of the grip body, therefore the finger indents are not angled relative to each other to form various angles of orientation and/or various radii of curvature for each of the user's fingers when in relaxed positions. Further, the grip body does not include a thumb indent which is angled on a surface opposed from the finger indents, thereby detracting from comfortable holding of the grip body over long periods of time.

Mainiero, in the '008 patent, discloses a golf grip training and exercise device designed for short periods of gripping by either a right or left hand. The golf grip includes a body having symmetrical right and left halves and having an oval cross-section which retains the same diameter and width along the length of the body. The right and left halves are mirror images, with three finger indentations and a thumb indentation in generally the same positions on either half, therefore allowing gripping in a right or a left hand. Due to the limits to the number of indentations, at least one finger is not accommodated in an indentation on the right or left halves during gripping exercises. Further, by maintaining the same diameter and width along the length of the golf grip body, the lesser curved radius of the little finger is not readily accommodated by the finger end of the golf grip, even though the golf grip is utilized over short periods of time.

An ambidextrous hand orthosis is disclosed by Betcher in the '168 patent, providing a hand orthosis having an oblate spheroid shape on which the patient's fingers are positioned in separate finger groove in order to separate the fingers from the patient's palm during sterile medical procedures. The hand orthosis includes two thumb grooves parallel and adjacent to opposed sides of finger grooves, and includes means for fastening of a pair of overlapping connectable straps for encircling the patient's wrist when the hand orthosis is positioned between the patient's fingers and palm. The oblate spheroid shape of the hand orthosis is appropriate for most adult patients undergoing medical procedures, but alternative shapes are needed for young patients with small hands and/or aged patients with arthritic hands and who undergo extended and repetitive periods of rehabilitative procedures.

There exists a need to provide a hand held orthosis which is readily sterilized for use in a surgical setting, and provides separation of each finger from adjacent fingers while preventing the fingers from contacting the palm of the hand. Further, a need exists for a hand held orthosis configured for retention for extended time periods in a hand disposed in a relaxed orientation for a patient undergoing surgical procedures on an upper extremity or a person undergoing rehabilitation of either hand and/or fingers. In addition, a need exists for a hand held orthosis configured for retention in each hand over extended time periods for a comatose patient or a patient in a geriatric setting.

BRIEF SUMMARY OF THE INVENTION

According to one embodiment of the present invention, a hand orthosis is disclosed for support of a patient's thumb and fingers in spaced apart orientation and separated from contact with the patient's palm or inner wrist. The hand orthosis includes an elongated body having about three circumferential sections including a palmar surface, an adjacently disposed thumb support surface, and a finger support surface opposed from the palmar surface. The elongated body includes a plurality of unequal diameters spaced apart and distributed along its major axial length extended from a distal end, through a mid-segment, and ending at a base end positionable against the patient's palm proximal of but apart from the wrist.

A plurality of finger concavities are angled in helical orientation across the finger support surface, the finger concavities include a first or index finger concavity angled toward the distal end, a second and third finger concavity angled across the mid-segment, and a fourth finger concavity angled toward the base end. Each finger concavity is angled to be non-perpendicular relative to the major axial length of the elongated body.

A thumb concavity originates proximal of the mid-segment and adjacent of the palmar surface, with the thumb concavity angled to extend proximal of the distal end. The angle of the thumb concavity is substantially opposed in orientation from the index finger concavity, such that the thumb concavity readily cradles the patient's thumb in separation from the index finger and each of the patient's second through fourth fingers when in encircling relationship on respective thumb support and finger support surfaces of the elongated body.

The palmar surface of the elongated body is positioned against the patient's palm to allow each finger and the thumb to be cradled in spaced-apart, curved and relaxed orientation in respective concavities on the respective surfaces of the elongated body. The elongated body is retained between the patient's palm, thumb, and fingers when each are maintained in spaced apart and relaxed orientation. The elongated body remains within the patient's hand whether the fingers are clenched in repetitive constricting movements to grip the body, or the fingers remain relaxed but curved around the elongated body. The hand held orthosis does not impede lateral or pivoting movements of the hand relative to the wrist due to the lack of an attaching member extended from the elongated body base end for contacting against the patient's wrist. A method of use is also disclosed for utilizing the hand held orthosis in sterile surgical environments, in a rehabilitative environment with young patients having small hands, and/or with aged patients having arthritic hands and undergoing long term rehabilitation.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 2A:
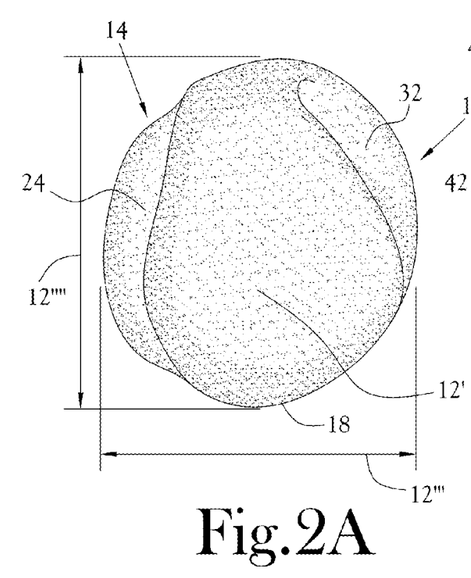
FIG. 2A is a distal end view of the hand orthosis of FIG. 1A, illustrating the asymmetric oval diameters of the distal end of the orthosis.
Figure 2B:
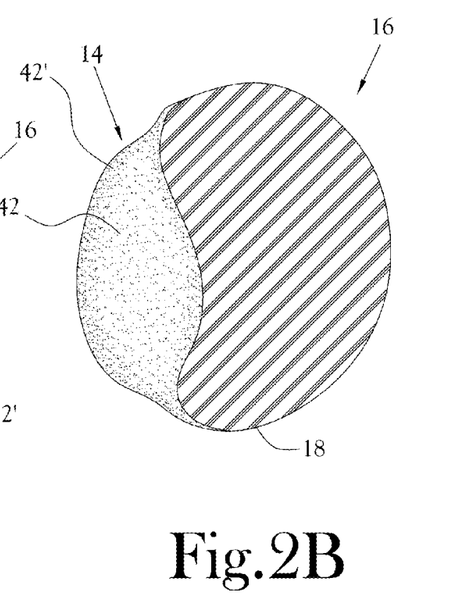
FIG. 2B is a section view along 2B-2B of FIG. 1A, illustrating the distal end contours which cradle the thumb apart from a forefinger and the palm of the hand.
Figures 2C, 2D:
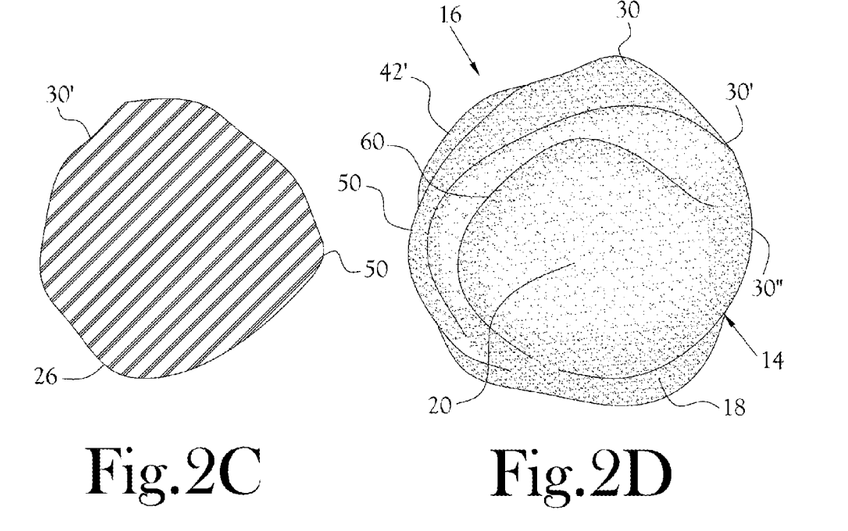
FIG. 2C is a section view along 2C-2C of FIG. 1A, illustrating contours of a mid-portion which cradle each finger apart from the palm of the hand.
FIG. 2D is a base end view of the hand orthosis of FIG. 1A.
Figure 3:
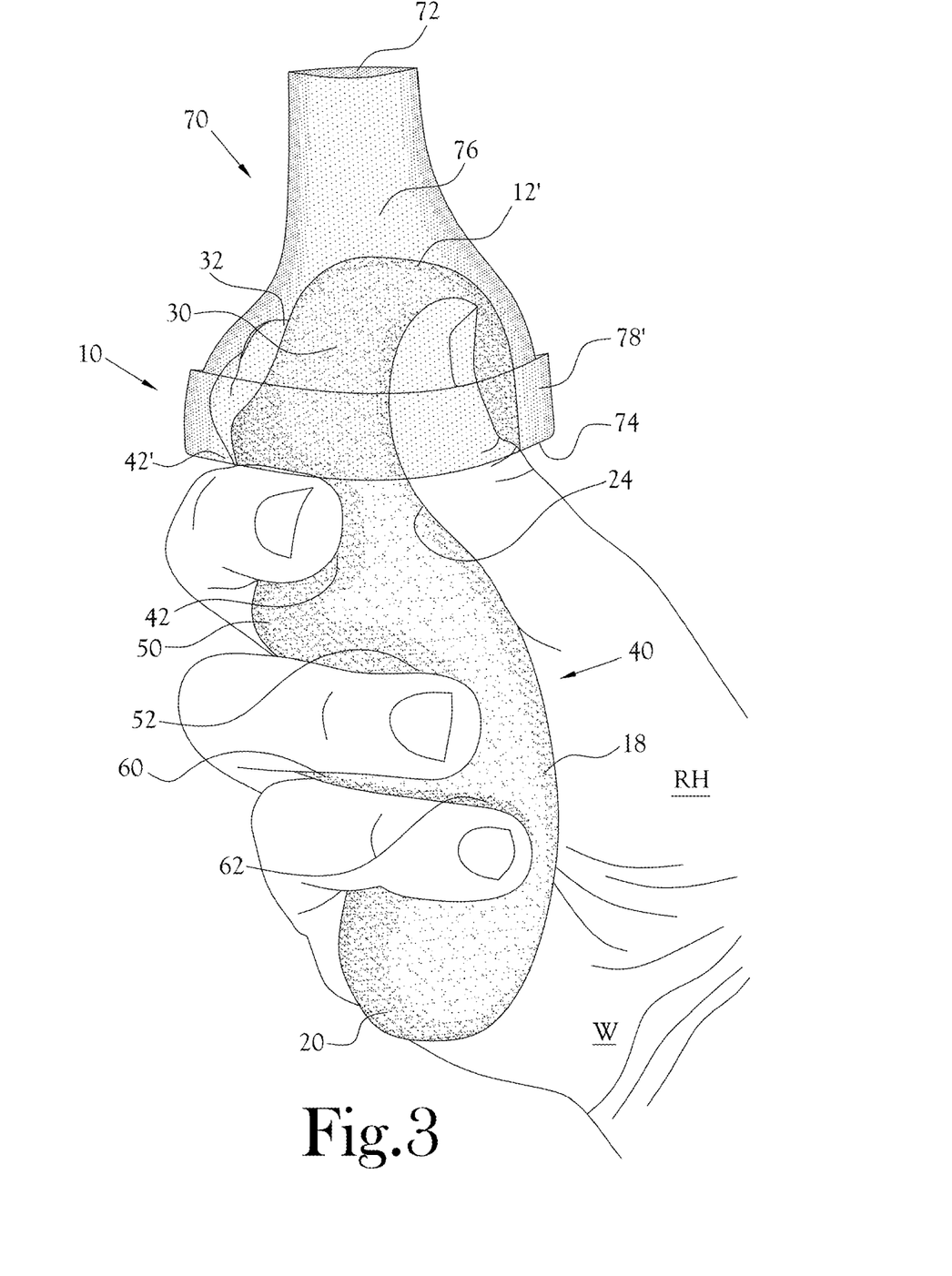
FIG. 3 is a side view of a hand orthosis within a right-hand and having a flexible enclosure partially covering a thumb, forefinger, and an orthosis distal end.
Figure 5:
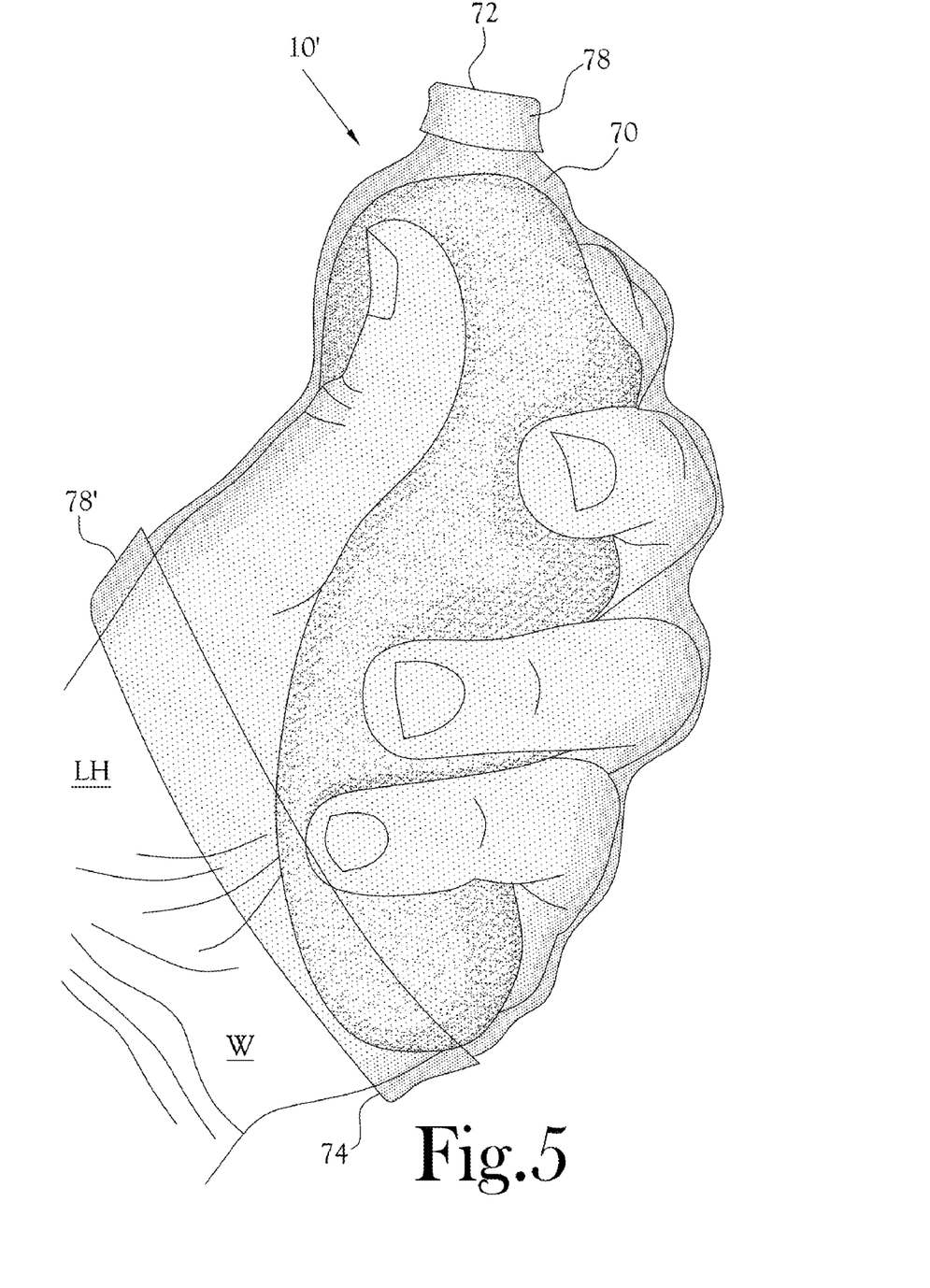
FIG. 5 is a perspective view the left-hand orthosis of FIG. 4, illustrating the flexible enclosure covering the orthosis retained between the patient's palm and fingers in encircling orientation on the orthosis.
Figure 6:
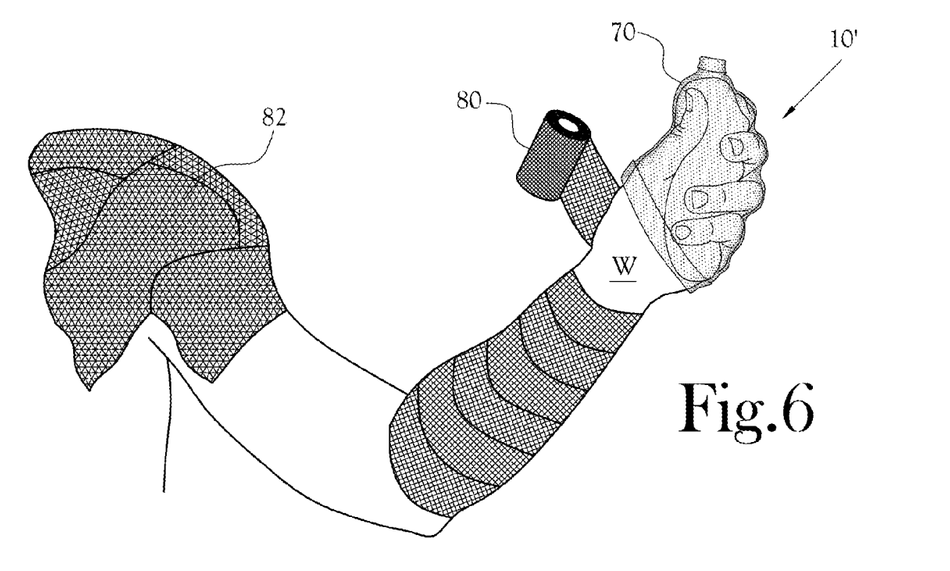
FIG. 6 is a perspective view of the left-hand orthosis of FIG. 5, illustrating the orthosis retained in the hand for wrapping with sterile material for surgery.
Figure 7:
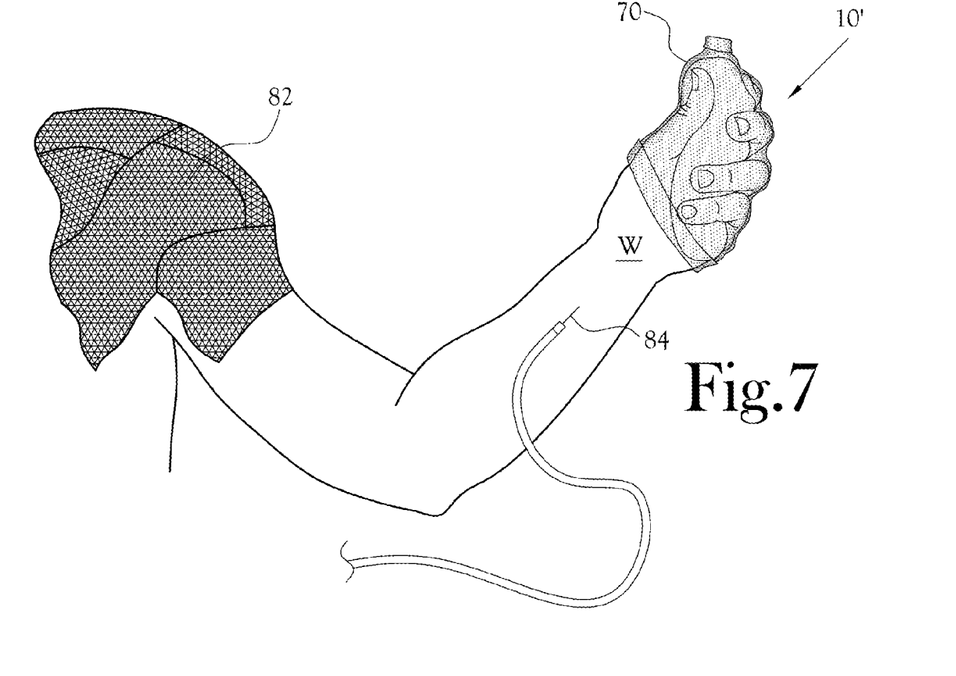
FIG. 7 is a perspective view of the left-hand orthosis of FIG. 6, illustrating the orthosis retained by the hand without impeding intravenous delivery of fluids.
Figure 8:
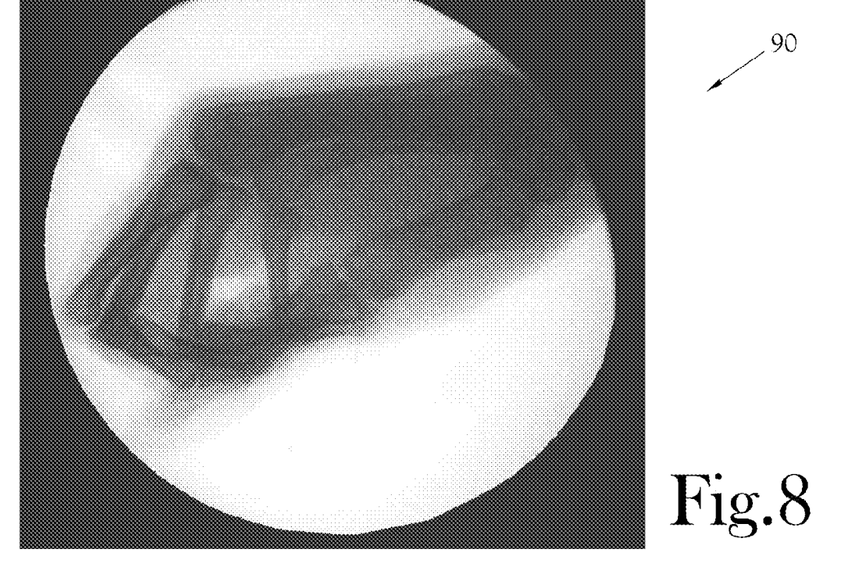
FIG. 8 is a side view of a patient's hand after surgery performed without use of the hand held orthosis of the present invention.
Figure 9:
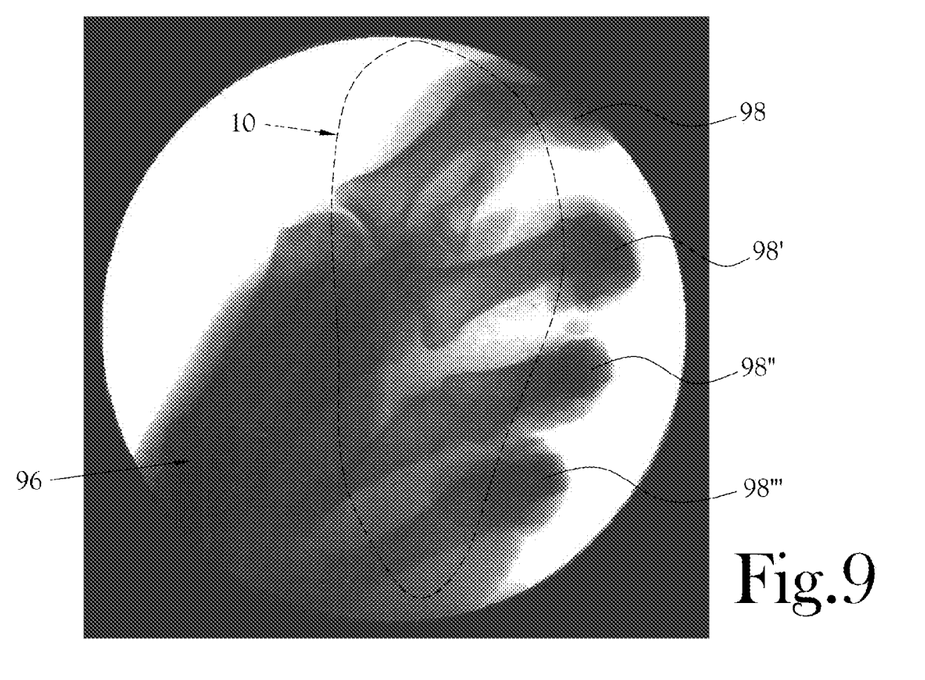
FIG. 9 is a side view of a patient's hand after surgery performed with use of the hand held orthosis of the present invention.

A hand orthosis 10 is disclosed for support of a patient's thumb and fingers in spaced apart orientation and separated from contact with the patient's palm and inner wrist surfaces. The hand orthosis 10 is configured in a right-handed embodiment (see FIGS. 1A, 1B, and 3), and a left-handed embodiment 10' (see FIGS. 4-6). The right-handed and left-handed embodiments are mirror images of each other to accommodate either hand and respective thumb and finger digits, therefore much of the following discussion will be referencing the right-handed embodiment. Each hand orthosis 10 10' includes an elongated body 12 having a length-wise axis 12' extending from a bulbous shaped distal end 12' having a first width 22 of a first minor axis 12''', through a mid-portion having a second width 22' of a second minor axis, and ending at a base end 20 having a third width 22'' of a third minor axis of a lesser width than either the first width 22 or second width 22'. One of the unique features of the elongated body 12 includes the distal end 12' and base end 20 are shaped in non-symmetrical oval configurations when viewed from respective ends (see FIGS. 2A-2D). Another unique feature is the wide portion of first minor axis 12''' is rotated about thirty degrees from alignment with the second minor axis, which is rotated about thirty degrees from alignment with the wide portion of third minor axis of the base end 20 (see FIGS. 1A and 2D).

The elongated body 12 includes convoluted exterior surfaces consisting of three sectors of curved surfaces extending the length of the orthosis 10, 10', including a thumb support surface 14 curving to join with a palmar surface 18, which curves to join with a finger support surface 16 extending radially to join with the thumb support surface 14. Along its major axial length 12'', the elongated body 12 includes at least three areas of different cross-sectional areas and each area having a minor width axis which is rotated to not be aligned with either adjacent minor width axis of the elongated body 12. The distal end 12' includes a rounded end which expands to a first width 22' of about two inches and a depth 22" of about two inches proximal of the distal portion of the thumb concavity 24 and the distal portion of the index finger concavity 32 (see FIGS. 2A and 2B). A second width 22' of about one and three-quarter inch is proximal of a mid-segment 40 (see FIG. 2C). The second width 22' is measured along a second minor width axis which is rotated about thirty degrees from alignment with the minor width axis of the first width 22. A third width 22" is measured along a third minor width axis proximal of the base end 20 (FIG. 2D), and is rotated between about eighty to about ninety degrees. The base end 20 is sized in width to allow the little finger to encircle the end without contacting the base of the thumb. The base end 20 length extends past an encircling little finger during use, and is sized to fit against the base of the palm base and proximal of, but not contacting, the inner wrist W surface of the patient. Alternative width and length dimensions are utilized for an elongated body 12 used with large hands or small hands.

The contour of the thumb concavity 24 originates 26 proximal of the mid-segment 40 adjacent to the palmar surface 18, and is angled across the thumb surface 14 to end 28 proximal of the distal end 12'. An angle 28' of about thirty degrees from the major axis 12" provides for a patient's thumb to be readily cradled in a relaxed orientation by the thumb concavity 24. The thumb cradled by concavity 24 is directed toward the end of the patient's index finger when the finger is cradled in the second concavity 32, while both index finger and thumb are in opposed encircling relationship on respective finger support surface 16 and thumb support surface 14 of the elongated body. A properly sized orthosis 10, 10' will maintain separation of a thumb from the end of the index finger by a lengthwise curved ridge 30, 30', 30" of resilient material which extends longitudinally from the distal end 12' to end proximal of the base end 20.

Figure 1A:
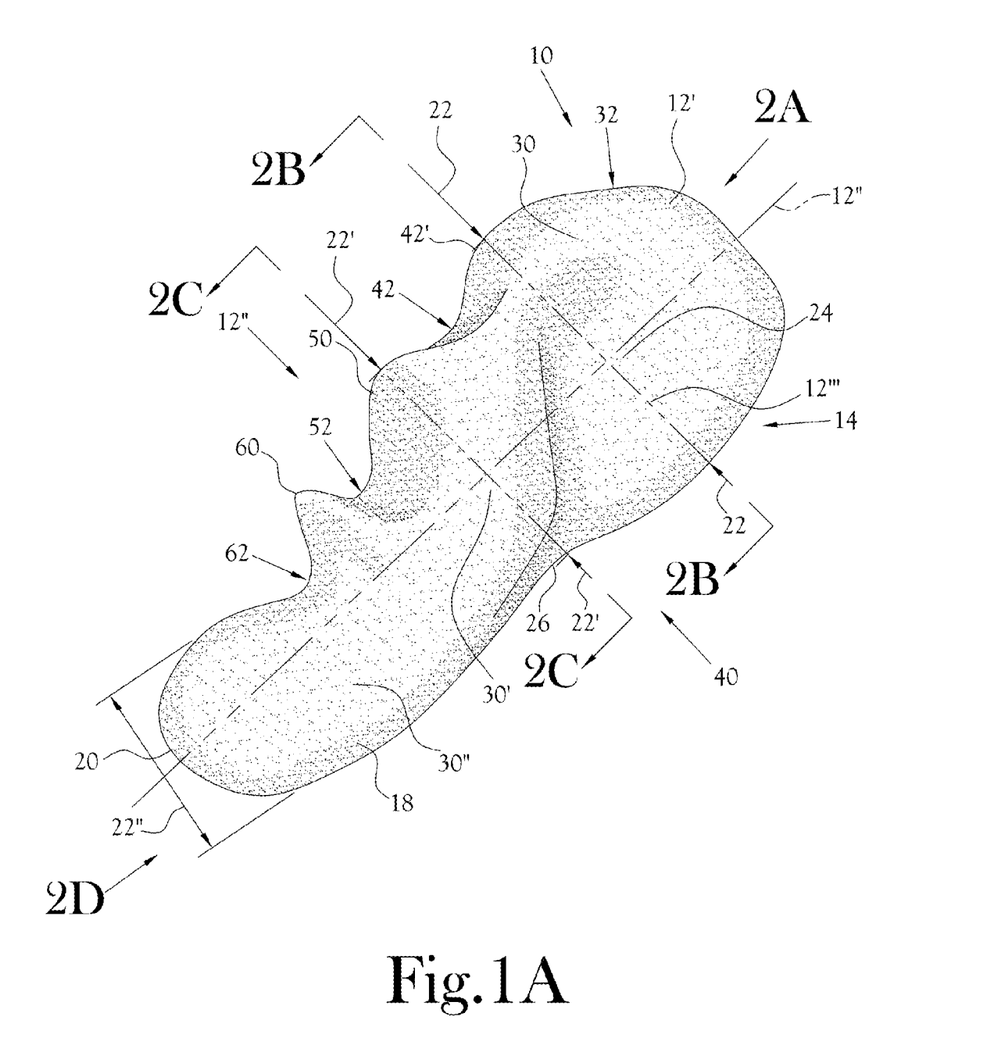
FIG. 1A is a perspective view of a right hand orthosis of the present invention, illustrating a plurality of contours for maintaining separation of the patient's thumb and fingers in encircling orientation within each separate contour.
Figure 1B:
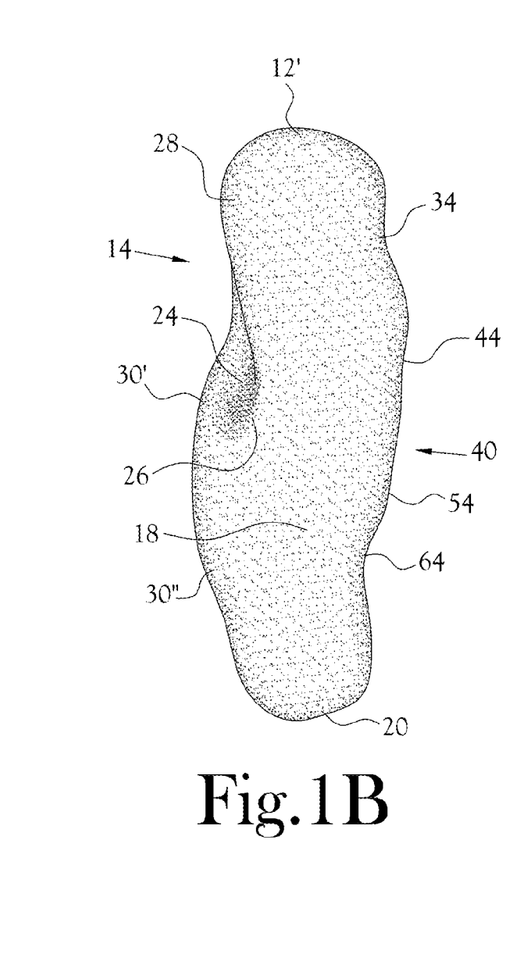
FIG. 1B is a palm side view of the hand orthosis of FIG. 1A.
Figure 1C:
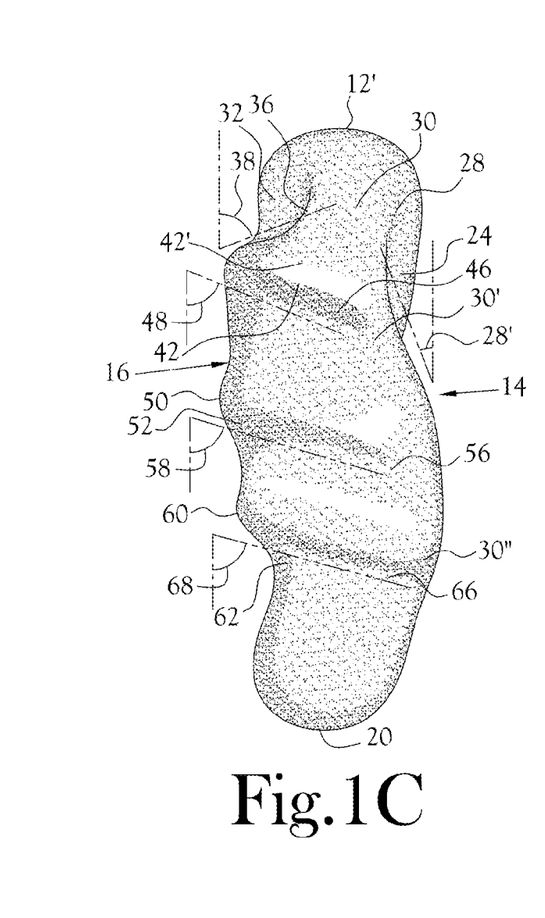
FIG. 1C is a side view of the finger support surface of FIG. 1A.
Figure 4:
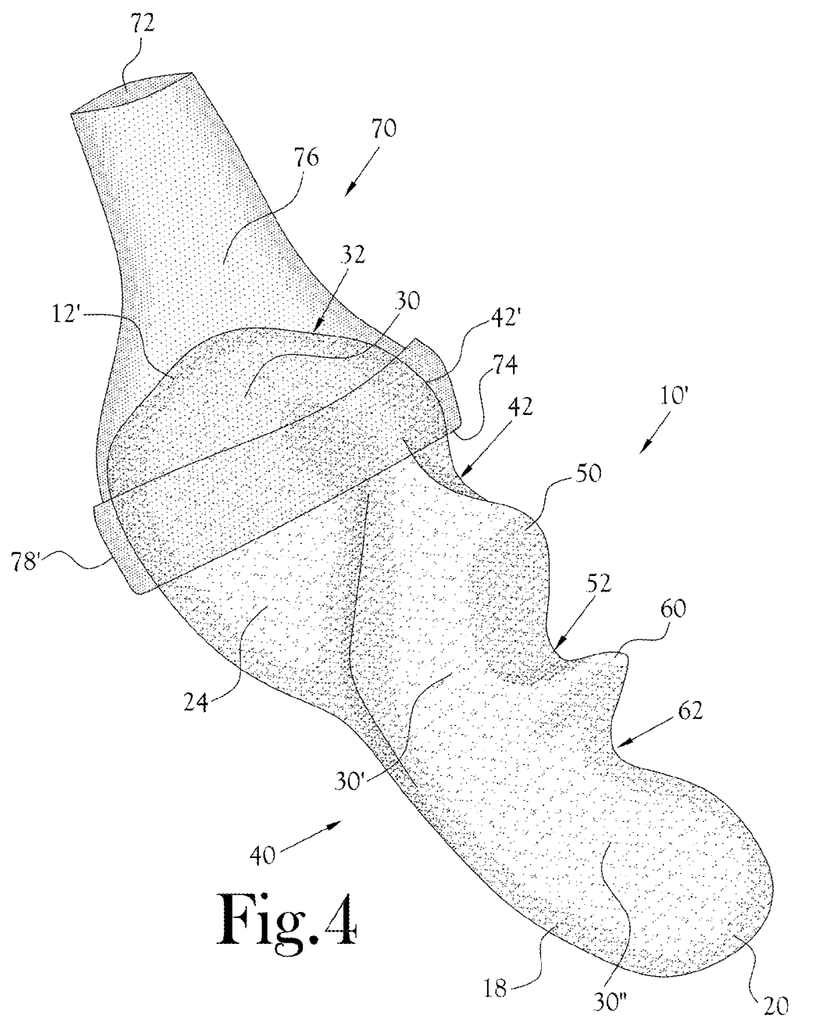
FIG. 4 is a perspective view of a left-hand orthosis having a flexible enclosure partially covering an orthosis distal end.

In order to separately cradle each finger and to maintain separation of the patient's fingers from the palm of the hand, a plurality of finger concavities 32, 42, 52, 62 are oriented in angled and generally helical orientation across the finger support surface 16 (see FIGS. 1A, 1C and 4). The index finger concavity 32 originates 34 proximal of a distal end of the palmar surface 18 and is curved opposite of the thumb concavity 24 with termination 36 proximal of the distal end 12'. The index finger concavity 32 is angled 38 about thirty degrees from the major axis 12" and toward the distal end 12'. A second finger concavity 42 is separated by a second ridge 42' apart from the index finger concavity 32. The second finger concavity 42 originates 44 proximal of the palmar surface 18, curves to a termination 46 proximal of the thumb surface 14, and is angled 48 across the mid-segment 40 toward thumb concavity 24 but is separated therefrom by an extension of lengthwise ridge 30, 30' (see FIGS. 1A and 1C). A third finger concavity 52 is separated by a third ridge 50 from second finger concavity 42. The third finger concavity 52 originates 54 proximal of the palmar surface 18, curves to a termination 56 proximal of the mid-segment 40, and is angled 58 across a middle portion of the finger support surface 16. A fourth finger concavity 62 is separated by a fourth ridge 60 from third finger concavity 52. The fourth finger concavity 62 originates 64 proximal of the palmar surface 18, curves to a termination 66 proximal of the base end 20, and is angled 68 toward the base end 20. Each finger concavity is angled to form a curved surface which is not generally perpendicular relative to the major axial length 12" to accommodate curvature of a patient's thumb and fingers cradled in respective concavities 24, 32, 42, 52, 62.

The palmar surface 18 of the elongated body 12 is positioned against the patient's palm to allow each finger and the thumb to be cradled in spaced-apart, curved and relaxed orientation in respective concavities on the respective surfaces of the elongated body. The elongated body 12 is inherently retained between the patient's palm, thumb, and fingers when the fingers and thumb are maintained in spaced apart and relaxed orientation. The elongated body 12 also is retained within the patient's hand whether the fingers are clenched in repetitive constricting movements to grip the body, or the fingers remain relaxed but curved around the elongated body. The hand held orthosis 10, 10' does not impede lateral or pivoting movements of the hand at the wrist due to a lack of attaching members or straps extended from the base end 20 for contacting the wrist.

Each adjacent thumb and finger concavity 24, 32, 42, 52, 62 is separated by a plurality of non-aligned ridges 30, 30', 30", 50, 60 on the surface of the elongated body 12 for maintaining separation of each finger apart from adjacent fingers, maintaining each finger apart from the thumb, and each digit maintained apart from the palm of the hand. The spaced apart configuration of the patient's fingers, thumb, and palm is maintained regardless of the patient being semi-conscious or unconscious, and regardless of involuntary hand or finger movements during surgery, physical therapy, or while the patient is reclining.

A tubular enclosure 70 is utilized to cover at least a portion of the elongated body when positioned between the patient's palm, fingers and thumb, in order to assure the patient does not throw or drop the orthosis 10, 10' during surgery or physical therapy. The tubular enclosure 70 is composed of expandable material and includes opposed open 72, 74 which are spaced apart by a sufficient length to enclose the orthosis from the distal end 12' to the base end 20, while the patient's hand is holding the orthosis. The opposed ends 72, 74 have an expandable diameter of sufficient flexibility to adequately stretch during a step of covering the orthosis held by the hand, with resilient rebound of the ends 72, 74 and body 76 to form an enclosure over the elongated body 12 having the patient's thumb and fingers positioned in respective thumb and finger concavities. The tubular enclosure 70 is also expandable in length orientations to fully enclose the patient's hand to about the base of the palm. The tubular enclosure 70 is sufficiently flexible to allow overlapping upon itself at either end 72, 74 to provide adequate material for maintaining coverage the hand from the fingers to the base of the palm, if the patient inadvertently or consciously attempts to remove the tubular enclosure 70. Removal of the tubular enclosure 70 from covering the elongated body 12 and hand is readily accomplished either by removal from the distal end 12' of the elongated body 12, or by rolling or sliding onto the patient's wrist W to allow visual examination of the patient's hand or palm without complete removal of the tubular enclosure 70. In addition, either end 72, 74 is partially retracted toward the mid-segment 22' diameter, thereby releasing one or more of the patient's thumb, first finger, or the base of the palm for inspection and medical treatment of the uncovered portions of the patient's fingers or hand while maintaining the elongated body between the fingers or positioned against the palm of the patient's hand. Lengths of the elongated body 12 and tubular enclosure 70 are selected to approximate the length between a forefinger when in relaxed orientation and the base of the palm, typically about four inches to about six inches, in order to not impede lateral movements or a range of motion of the patient's wrist W. Prior hand exercise devices have been sized to extend in resting relationship against the holder's wrist, or prior hand and finger immobilizers have included a wrist strap which connects one end of the immobilizer to the patient's wrist while partially limiting the rotational movement of a hand relative to a wrist.

The elongated body 12 includes an outer surface which is substantially sealed and impervious to absorption of body fluids or medicinal fluids, thereby allowing the outer surface to be sterilized upon application of commonly used sterilizing fluids. The interior of the elongated body 12 may be composed of porous, flexible materials is composed of a resiliently compressible material such as foam, rubber, or a low-density polymer which is transparent to electromagnetic radiations including X ray frequencies. The bone structure and positioning of the patient's fingers and thumb relative to the palm and hand can be ascertained by X-ray technology including computerized axial tomography while the hand is enclosed in surgical coverings and opaque wrappings.

A method of utilization for a right-handed and a left-handed hand orthosis 10, 10' includes a step of providing an elongated body 12 of flexible material including unequally curved first, second and third portions of the circumferential surface of the body 12, providing: (a) a palmar surface 18 extended approximately a first-third of the circumference of the body 12, (b) an adjacently disposed thumb support surface 14 having a thumb concavity 24 angled across approximately a second-third of the circumference of the body 12, and (c) a finger support surface 16 having a plurality of separate finger concavities 32, 42, 52, 62 angled across approximately a third-third or a half of the circumference of the body 12, opposed from the palmar surface 18, and spaced apart from the thumb concavity 24. The step of providing includes the elongated body 12 being configured to have a plurality of unequal cross-sectional areas (see FIGS. 2A-2C), which are spaced along a major axial length 12" of the body 12 between a distal end 12', a mid-segment 40 and a base end 20.

The method of use for the hand held orthosis 10, 10' further includes a step of gripping the orthosis 10, 10' elongated body 12 by a conscious patient, or alternatively positioning the orthosis 10, 10' in the patient's palm with respective finger and thumb digits encircling the orthosis 10, 10' in separate concavities for a semi-conscious patient or an unconscious patient. The configuration of the orthosis 10, 10' facilitates the continued gripping of the elongated body in each hand when the finger and thumb digits are curved in a relaxed orientation regardless of whether the patient is conscious or not. The steps of gripping or positioning the orthosis 10, 10' include maintaining each finger digit separated from adjacent finger digits, maintaining the thumb digit separate from each finger digit, and maintaining the finger and thumb digits separate and spaced-apart from the palm of the patient's hand. The method of use for the hand held orthosis 10, 10' is utilized in numerous ways, including: (a) in surgical, sterilized settings extending over numerous hours, (b) overnight for sleeping patients recuperating from surgery on an upper extremity, (c) in physical therapy settings extending over numerous hours of therapy repeated over many days, weeks and months, and (d) in convalescing homes or senior citizen nursing homes for semi-conscious or unconscious patients requiring protection from finger and thumb digits clinching against the palm of each hand. The steps of gripping or positioning further include maintaining the gripping relationship with the thumb and finger digits separated and spaced-apart from the palm, whether the patient's thumb and finger digits are curved in relaxed orientation, or are tensioned in voluntary or involuntary clinching orientation about the elongated body 12, without allowing contact between thumb and finger digits against the palmar surface or inner wrist.

The method of use further includes encircling the fingers and thumb positioned in gripping relationship around the elongated body with a tubular, flexible enclosure 70 lacking any additional connector straps or other means for fastening. The step of encircling with the enclosure 70 is utilized to encircle the distal end 12', the thumb and the forefinger, or to encircle the full length of the elongated body 12 and the thumb and all fingers, without impeding motions of the hand and wrist. Alternatively, the step of encircling can include the enclosure 70 extended in an overlapping configuration 78 from covering of the wrist, for coverage of the fourth and third finger digits and the base end 20 of the body 12, while leaving the forefinger and/or thumb digits encircling the distal end 12' without binding the patient's finger and/or thumb digits to the distal end 12', in order to allow surgical procedures applied to the thumb and/or forefinger, or to allow physical therapy performed on the thumb, forefinger, and/or second finger digits. The surgical procedures accomplished on the upper extremities and the shoulder of the patient may include the step of wrapping with a sterilized elastic wrap 80, for further enclosing the orthosis 10, 10' having the finger and thumb digits gripping thereon, and having the enclosure 70 encircling at least one end of the orthosis 10, 10' having the patient's fingers and thumb thereon. The step of wrapping is accomplished without disturbing a potential intravenous (IV) site 84 on the wrist or forearm, and without disturbing surgical coverings on a shoulder 82 and/or upper arm. One skilled in the art will recognize additional uses for the hand held orthosis 10, 10' and enclosure 70 for isolation of each finger and thumb digit from contacting each other, and/or from contacting the palmar surface or the inner wrist of the patient.

From the foregoing description, the hand held orthosis 10, 10' includes various unique functions. The function of compressibility is implemented by the elongated body 12 being composed of resiliently compressible material such as foam, rubber, or a polymer. The function of use in a sterile environment is provided by the elongated body 12 having an outer surface which is sealed and generally impervious, while the interior of the elongated body 12 may be composed of porous, flexible and resilient material. The function of maintaining separation of the fingers and thumb apart from the palm of the patient's hand is accomplished by the combination plurality of concavities 24, 32, 42, 52, 62 and the plurality of ridges 30, 30', 30", 50, 60 on the surface of the elongated body 12. The function of maintaining the orthosis 10, 10' in a hand in a relaxed orientation with curved fingers is accomplished by the convoluted surface features, the varying widths 22, 22', 22" along the length axis 12", and the rotated orientation of the minor width axis 12'" of distal end 12' relative to the minor width axis 20' of base end 20.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned invention, I claim:

1. A hand orthosis for maintaining separation between a patient's thumb, fingers, and palm, said hand orthosis comprising:

an elongated body having an upper end and a lower end;

a middle finger concavity formed in said elongated body, said middle finger concavity originating at a first point on said and terminating at a second point on said elongated body, said second point being lower on said elongated body than said first point;

a ring finger concavity formed in said elongated body, said ring finger concavity substantially parallel to said middle finger concavity, said ring finger concavity separated from said middle finger concavity by a first ridge;

a little finger concavity formed in said elongated body, said little finger concavity substantially parallel to said ring finger concavity, said little finger concavity separated from said ring finger concavity by a second ridge;

an index finger concavity formed in said elongated body, said index finger concavity bounded along one side and separated from said middle finger concavity by a third ridge, said index finger concavity bounded along an opposite side by a fourth ridge, said index finger concavity having an original end and a terminal end, said terminal end being closer to said upper end of said elongated body than said original end; and a thumb concavity formed in said elongated body, said thumb concavity having an original end proximate to said middle finger concavity and a terminal end proximate said elongated body upper end, said thumb concavity terminal end directed toward said index finger concavity terminal end, said thumb concavity terminal end and said fourth ridge proximate to said index finger concavity terminal end being substantially equidistant from said upper end, said thumb concavity terminal end separated from said index finger concavity terminal end by a fifth ridge.

2. The hand orthosis of claim 1 wherein said elongated body has a first perimetrical length of a first cross-sectional area taken through said middle finger concavity, a second perimetrical length of a second cross-sectional area taken through said ring finger concavity, and a third perimetrical length of a third cross-sectional area taken through said little finger concavity, said first perimetrical length and said second perimetrical length being greater than said third perimetrical length.

3. The hand orthosis of claim 2 wherein said first perimetrical length is greater than said second perimetrical length.

* * * * *